(12) United States Patent
Bernachon et al.

(10) Patent No.: US 10,149,895 B2
(45) Date of Patent: Dec. 11, 2018

(54) COMPOSITION FOR THE TREATMENT OF PROGRESSIVE RENAL DISEASES

(71) Applicant: VIRBAC, Carros (FR)

(72) Inventors: Natalia Bernachon, Nice (FR); Patricia Monginoux, Villeneuve Loubet (FR)

(73) Assignee: VIRBAC, Carros (FR)

(*) Notice: Subject to any disclaimer, the term of this patent is extended or adjusted under 35 U.S.C. 154(b) by 0 days.

(21) Appl. No.: 14/900,986

(22) PCT Filed: Jun. 26, 2014

(86) PCT No.: PCT/IB2014/062624
§ 371 (c)(1),
(2) Date: Dec. 22, 2015

(87) PCT Pub. No.: WO2014/207694
PCT Pub. Date: Dec. 31, 2014

(65) Prior Publication Data
US 2016/0144005 A1    May 26, 2016

(30) Foreign Application Priority Data
Jun. 27, 2013  (EP) .................................. 13174079

(51) Int. Cl.
| | |
|---|---|
| *A61K 33/06* | (2006.01) |
| *A61K 38/55* | (2006.01) |
| *A61K 45/06* | (2006.01) |
| *A61K 31/122* | (2006.01) |
| *A61K 31/202* | (2006.01) |
| *A61K 31/352* | (2006.01) |
| *A61K 31/375* | (2006.01) |
| *A61K 31/59* | (2006.01) |
| *A61K 31/715* | (2006.01) |
| *A61K 31/722* | (2006.01) |
| *A61K 9/00* | (2006.01) |
| *A61K 35/20* | (2006.01) |
| *A61K 35/60* | (2006.01) |
| *A61K 36/185* | (2006.01) |
| *A61K 36/481* | (2006.01) |
| *A61K 36/708* | (2006.01) |
| *A61K 47/36* | (2006.01) |

(52) U.S. Cl.
CPC .......... *A61K 38/556* (2013.01); *A61K 9/0056* (2013.01); *A61K 31/122* (2013.01); *A61K 31/202* (2013.01); *A61K 31/352* (2013.01); *A61K 31/375* (2013.01); *A61K 31/59* (2013.01); *A61K 31/715* (2013.01); *A61K 31/722* (2013.01); *A61K 33/06* (2013.01); *A61K 35/20* (2013.01); *A61K 35/60* (2013.01); *A61K 36/185* (2013.01); *A61K 36/481* (2013.01); *A61K 36/708* (2013.01); *A61K 45/06* (2013.01); *A61K 47/36* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 2005/0124591 A1 | 6/2005 | Tian et al. | |
| 2009/0269399 A1* | 10/2009 | Lewis | A61K 9/4891 |
| | | | 424/452 |

FOREIGN PATENT DOCUMENTS

| | | |
|---|---|---|
| WO | 96/31130 A3 | 10/1996 |
| WO | 2006061336 A3 | 6/2006 |

OTHER PUBLICATIONS

Zatelli et al. ("Effect of Dietary Supplements in Reducing Probability of Death for Uremic Crises in Dogs Affected by Chronic Kidney Disease (Masked RCCT)", The ScientificWorld Journal, Epub Apr. 19, 2012; pp. 1-7).*
Thomason (Kidney Disease in Dogs, The Whole Dog, 2012, pp. 1-12; obtained from http://www.grrsn.org/blog/kidneydiseaseindogs/ on Jun. 23, 2017).*
Peng et al. ("Herbal Treatment for Renal Diseases", Ann Acad Med Singapore 2005; pp. 44-51).*
Bernachon et al., "Effect of a Product Containing the Dietary Phosphate Binders Calcium and Magnesium Carbonate Associated with Other Reno-protectant Substances (Pronefra®) on Blood Parameters and Mineral Balance in Adult Cats", Intern J Appl Res Vet Med., 2014, 8-17.*
Spiegel et al., "Magnesium Carbonate is an Effective Phosphate Binder for Chronic Hemodialysis Patients: A Pilot Study", Journal of Renal Nutrition, 2007, pp. 416-422 (Year: 2007).*
Parsons et al., "Successful Control of Hyperparathyroidism in Patients on Continuous Ambulatory Peritoneal Dialysis Using Magnesium Carbonate and Calcium Carbonate as Phosphate Binders", Nephron, 1993, pp. 379-383 (Year: 1993).*
Thomason, Kidney Disease in Dogs, The Whole Dog, 2012, pp. 1-12; obtained from http://www.grrsn.org/blog/kidneydiseaseindogs/ on Jun. 23, 2017), (Year: 2012).*
Peng et al., "Herbal Treatment for Renal Diseases", Ann Acad Med Singapore 2005; pp. 44-51 (Year: 2005).*
Zatelli et al., "Effect of Dietary Supplements in Reducing Probability of Death for Uremic Crises in Dogs Affected by Chronic Kidney Disease (Masked RCCT)", The Scientific World Journal, Epub Apr. 19, 2012; pp. 1-7 (Year: 2012).*
International Search Report dated Sep. 3, 2014 corresponding to International Patent Application No. PCT/IB2014/062624, 4 pages.
"Ipakitine—a unique formulation that your pet will benefit from," Internet Citation, Jul. 23, 2010, Retrieved from the Internet: URL:http://www.vetoquinol.com.uk/downloadable/GuideToKidneyFailure.pdf [retrieved on Oct. 29, 2013], pp. 1-2.

(Continued)

*Primary Examiner* — Lianko G Garyu
(74) *Attorney, Agent, or Firm* — Dentons US LLP (57) ABSTRACT

Described herein is an association of at least one phosphate binder, at least one uremic toxin binder, at least one vasoactive antihypertensive agent and at least one antifibrotic agent for the management of progressive renal diseases including chronic kidney diseases (CKD) in domestic carnivores. Specifically, the application describes veterinarian compositions comprising such an association and the use thereof for the treatment of CKD conditions.

4 Claims, 4 Drawing Sheets

(56) References Cited

OTHER PUBLICATIONS

Li, X., et al., "Chinese Herbal Medicine in the Treatment of Chronic Kidney Disease," Advances in Chronic Kidney Disease, vol. 12, No. 3, Jul. 2005. pp. 276-281.

Zhang, J., et al., "Systematic review of the renal protective effect of *Astragalus membranaceus* (root) on diabetic nephropathy in animal models," Journal of Ethnopharmacology, vol. 126, No. 2, Nov. 2009, pp. 189-196.

"Tensix—Cardiovascular—SuperSmart," Internet Citation, Oct. 20, 2013, Retrieved from the Internet: URL:http://www.supersmart.com/en - - Cardiovascular - - Tensixa%EF%BF%BD%C2%A2% - - 0552 [retrieved on Oct. 20, 2013], pp. 1-2.

* cited by examiner

COMPOSITION FOR THE TREATMENT OF PROGRESSIVE RENAL DISEASES

CROSS-REFERENCE TO PRIOR APPLICATIONS

This application is a National Stage of PCT/IB2014/062624, filed Jun. 26, 2014, and designating the United States (published in English on Dec. 31, 2014, as WO 2014/207694A1), which claims priority under 35 U.S.C. § 119 to European Patent Application No. 13174079.7, filed Jun. 27, 2013, each hereby expressly incorporated by reference in its entirety and each assigned to the assignee hereof.

The present invention concerns the management of progressive renal diseases including chronic kidney diseases (CKD) in domestic carnivores. Specifically, the present invention is directed to veterinarian compositions associating several active ingredients and use thereof for the treatment of CKD conditions.

CKD and ensuing renal failure is the most common kidney disease in domestic carnivores [S. Ettinger and E. Feldman, Textbook of Veterinary Internal Medicine Volume 2, St. Louis: ELSVIER SAUNDERS, 2005] diagnosed in 2-20% [Boyd et al., *J Vet Intern Med*, no. 22, pp. 1111-1117, 2008] of all cats regardless age, and up to 31% in geriatric cats older than 15 years [O. C. O. T. e. a. Lulich J P, "Feline renal failure: Questions, answers, questions," *Compend Contin Educ Pract*, no. 14, p. 127-152, 1992]. The condition is characterized by the presence of irreversible structural lesions in the kidney; clinical signs are not seen until at least ⅔rd of functional nephrons are lost, at this stage, said signs include weight loss, reduced appetite, dehydration, lethargy, polydipsia, polyuria, systemic hypertension, vomiting, anaemia, oral ulcers.

Clinical management of chronic kidney disease in pets has progressed a lot over the past 15 years, where new standards in diagnosis, understanding and treatment of this pathological condition have been set. Hyperphosphataemia has been recognized as a serious complication of chronic kidney disease (CKD) in cats. It is an important factor of progression [Syme et al., *J Vet Intern Med*, no. 20, pp. 528-535, 2006] and death from pathological renal conditions in cats [Chakrabarti et al., *J Ver Intern Med*, no. 26, pp. 275-281, 2012]. Other important prognostic and diagnostic factors have been recognized over the past 30 years, among them plasma levels of creatinine (SCr) [Syme et al., *J Vet Intern Med*, no. 20, pp. 528-535, 2006; Chakrabarti et al, *J Ver Intern Med*, no. 26, pp. 275-281, 2012; King et al., *J Vet Intern Med*, pp. 21:906-916, 2007].

Plasma creatinine and blood urea nitrogen (BUN) concentrations are commonly used as screening tests in veterinary practices; plasma creatinine and urea levels are negatively correlated with the glomerular filtration rate [Wagner et al., *Berl. Münch. Tierärztl. Wschr.*, no. 117, pp. 310-315, 2004]. Creatinine is a breakdown product of creatinine phosphate in mammalian muscle and it is usually produced by the body at a constant rate. It removed from the body by urine: the molecule is eliminated in a passive manner by the kidney without any interaction: creatinine is not reabsorbed by the kidney. The blood creatinine level depends on the ability of the kidneys to remove it and the muscle mass [Chakrabarti et al., *J Ver Intern Med*, no. 26, pp. 275-281, 2012]. Creatinine assessment gives an indication of the ability of renal filtration and renal health. Increased plasma creatinine concentration is associated with reduced survival time in cats suffering from renal disorders [King et al., *J Vet Intern Med*, pp. 21:906-916, 2007]. Urea is a protein breakdown product dissolved in the blood; it is normally excreted by kidneys. Urea accumulates in the blood of cats suffering from CKD, however this accumulation is not specific to kidney disease only, and it could increase following a protein-rich meal or by dehydration. BUN concentrations tend to correlate with clinical signs of uraemia. For practical purposes BUN may thus be viewed as a marker of retained uremic toxins.

Dietary phosphorus is absorbed from the gastrointestinal tract, it is freely filtered at the glomerulus and could be considered as a marker of glomerular filtration rate (GRF); in healthy animals, if the dietary intake of phosphorus remains constant so is the blood phosphorus level. In animals having renal disease a decline in the glomerular filtration rate will lead to phosphorus retention and hyperphosphatemia and consequently to renal hyperparathyroidism. Controlling the rise in phosphorus can dramatically suppress disease progression and extend life duration: the effective management of phosphorus levels in cats affected by CKD improves survival [Brown et al., *Intern J Appl Res Vet Med*, vol. 6, no. 3, 2008]. Hyperphosphatemia can be managed by dietary restriction [Plantinga et al., *The Veterinary Record*, vol. August 13, pp. 185.487, 2005], by administration of intestinal phosphate binders [Wagner et al., *Berl. Münch. Tierärztl. Wschr.*, no. 117, pp. 310-315, 2004; Brown et al., *Intern J Appl Res Vet Med*, vol. 6, no. 3, 2008] or both [Barber et al., *Journal of Small Animal Practice*, no. 40, pp. 62-70, 1999]. The dietary modification has been demonstrated to be a mainstay of the efficient disease containment [O. C. O. T. e. a. Lulich J P, "Feline renal failure: Questions, answers, questions.," *Compend Contin Educ Pract*, no. 14, p. 127-152, 1992; Syme et al., *J Vet Intern Med*, no. 20, pp. 528-535, 2006; Chakrabarti et al., *J Ver Intern Med*, no. 26, pp. 275-281, 2012; Wagner et al., *Berl. Münch. Tierärztl. Wschr.*, no. 117, pp. 310-315, 2004]; the effect of such dietary modification could nevertheless be improved as it has been previously demonstrated that intestinal phosphate binding agents administrated alone have no apparent effect on BUN, SCr, GFR, renal plasma flow, or proteinuria [Brown et al., *Intern J Appl Res Vet Med*, vol. 6, no. 3, 2008].

Because CKD cannot be diagnosed until significant lesions are present, it is not possible to identify and to prevent the early changes in this disease. Renal lesions in CKD are irreversible and there is no possibility to eliminate them. Therefore, there is a need for management options that could ameliorate the clinical signs of uraemia, minimize disturbances associated with excess or losses of electrolytes, and modify progression of renal failure in order to increase the quality of life of the animal and increase life expectancy.

Available products intended to manage CKD conditions include a composition comprising calcium carbonate and chitosan (Ipakitine® sold by Vetoquinol), this composition is to be administered along with regular food; unfortunately this composition is poorly appreciated by pets and does not lead to a reliable compliance. Moreover, the association of calcium carbonate and chitosan only provides a partial solution to the mentioned problems as the association of the two ingredients does not lead to management of creatinemia levels, contrarily the effects reported with the association according to the present invention.

Inventors have now developed a specific association of several active ingredients that shows an improved effect on CKD's markers, said association comprises at least a phosphate binder, at least an uremic toxin binder, at least a vasoactive antihypertensive agent and at least an antifibrotic agent. In addition to a beneficial effect on phosphatemia and on uremia, this association induces an unexpected decrease of plasma creatinine concentration, such a decrease has never been described before. It is also interesting to note that such association does not lead to any undesirable increase of calcemia.

The present invention thus relates to the association of:
at least one phosphate binder,
at least one uremic toxin binder,
at least one vasoactive antihypertensive agent and
at least one antifibrotic agent,
and to any composition comprising such ingredients.

Said association is particularly useful as veterinarian medicine, especially for inducing a decrease of plasma creatinine concentration and, more generally, for preventing and/or treating high blood pressure and/or maintaining blood pressure in normal ranges and/or progressive renal diseases in carnivore domestic animal, including dogs and cats.

Progressive renal diseases include chronic kidney diseases (CKD), chronic renal failure (CRF), chronic renal disease, kidney insufficiency, kidney failure, azotemia . . . .

Controlling serum phosphorus levels in patients with renal failure is critical; this can be done with the use of oral phosphate-binding agents allowing the decrease of phosphate absorption.

Phosphate Binders

The phosphate binders that can preferably be used in the association of the invention comprise three major classes of compounds:
calcium-based binders,
sevelamer hydrochloride, and
lanthanum carbonate.

As calcium-based binders can induce an undesired hypercalcaemia, other compounds can also be used, such as magnesium-based binders. One can also mention a newly developed phosphate binder: polynuclear Fe(III) starch/saccharose complex.

Preferred phosphate binders are calcium carbonate, magnesium carbonate and calcium acetate; those binders prevent phosphorus absorption in the digestive tract by forming insoluble calcium phosphate excreted in the faeces.

The association according to the present invention may comprise more than one phosphate binder, for example, two or three, preferably two phosphate binders.

According to a preferred embodiment, the association of the invention comprises a phosphate binder composed of calcium carbonate and of magnesium carbonate; preferably, the ratio calcium carbonate/magnesium carbonate is comprised between 3 and 4; more preferably, this ratio is 3.7.

Uremic Toxins Binders

A variety of uremic toxins are involved in the clinical symptoms of CKD such as indoxyl sulphate. The uremic toxin binders according to the present invention are preferably chosen amongst:
chitosan which is a natural polysaccharide obtained from the shells of crustaceans (shell fish such as crabs and shrimps); acting as an oral adsorbant, chitosan binds precursors of some uraemic toxins in the digestive tract. Chitosan is described to bind with the indoxyl, so it cannot be converted to indoxyl sulphate, thus reducing toxin levels;
coal;
arabic gum.

Vasoactive Antihypertensive Agents

The vasoactive antihypertensive agents according to the present invention are preferably chosen amongst:
Oligopeptides which have ACE (angiotensin converting enzyme)-inhibitory activity; hereafter named "ACE oligopeptides". Such oligopeptides can be of marine or milk origin. This category of vasoactive antihypertensive agents includes the following products:
purified marine peptides extracted from North Sea Leanby double enzymatic hydrolysis, said peptides create natural anti-ACE factors with moderate antihypertensive properties; they lower blood pressure by inhibiting ACE, thereby leading to vasodilatation; this product is sold under the name Protensin by the Company COPALIS;
a shellfish peptides hydrolysate from scallop extracts sold by the Company Phosphotech;
a mackerel peptides hydrolysate sold under the name Tensideal by the Company ABYSS;
a bonito peptides hydrolysate sold under the name Katsuobushi Oligopeptide by the Company NIPPON SUPPLEMENT;
Oligopeptides from milk origin which have ACE-inhibitory activity are for example, trippeptides Ile-Pro-Pro activated by enzymatic digestion of milk proteins sold under the name TENSGUARD by the Company DSM.

Vitamin C and derivatives thereof;
Omega 3;
Co-enzyme Q10;
Magnesium;
Flavonoïdes;
extracts of Ibiscus Sabdariffa.

Anfifibrofic Agents

The antifibrotic agents according to the present invention are preferably chosen amongst:
vitamin D and derivatives thereof;
extracts of *Rheum officinalis;*
polysaccharides extracted from *Astragalus membranaceus;*

*Astragalus membranaceus* (*Astragalus* root) belongs to the fabecean plant family and have anti-fibrotic and anti-inflammatory properties; its extracts are recommended to be used to support and maintain proper kidney function and mineral balance. Its anti-fibrotic activity has been demonstrated in multiple studies on rats resulting in a decrease in the loss of renal function and decreased histological damage (rat models with induced nephrosis). In addition reno-protective effects have also been demonstrated in human patients, leading to decreased proteinuria and decreased levels of creatinine. *Astragalus membranaceus*' polysaccharides have been shown to suppress the over-expression of pro-fibrotic factors (e.g. TGF-$\beta$1) and reduce the infiltration of inflammatory cells (e.g. macrophages) and the expression of pro-inflammatory cytokines (IL-2, IL-6, TNF-$\alpha$).

In a particular embodiment of the present invention, the ratios of the active ingredients of the association according to the invention are as follows:
the ratio between the vasoactive antihypertensive agent, preferably ACE oligopeptides, and the antifibrotic agent, preferably polysaccharides extracted from *Astragalus membranaceus*, is comprised between 2/1 and 1/5, preferably this ratio is about 1.25;
the ratio between the vasoactive antihypertensive agent, preferably ACE oligopeptides, and the uremic toxin binder, preferably chitosan, is comprised between 4/1 and 1/2, preferably this ratio is about 2;
the ratio between the vasoactive antihypertensive agent, preferably ACE oligopeptides, and the phosphate binder, is comprised between 2/1 and 1/2.

The present invention also relates to a veterinarian composition comprising the association as defined above and a physiologically acceptable vehicle.

The person skilled in the art will adapt the content of each active agent of said veterinarian composition depending on its specific nature and the target animal.

Usually, phosphate binders are used at a concentration comprised between 5 and 50 mg/kg/day, preferably between 10 and 20 mg/kg/day; the content of uremic toxin binders is comprised between 2 to 10 mg/kg/day, preferably between 4 and 8 mg/kg/day; the content of antifibrotic agents is comprised between 3 and 16 mg/kg/day, preferably between 5 and 15 mg/kg/day, and the content of the vasoactive antihypertensive agents is comprised between 5 and 50 mg/kg/day, preferably between 7 and 15 mg/kg/day.

In an embodiment, the present invention relates to a veterinarian composition comprising:
- at least one phosphate binder,
- at least one uremic toxin binder,
- at least one vasoactive antihypertensive agent, and
- at least one antifibrotic agent, wherein the phosphate binder is a mixture of calcium carbonate and of magnesium carbonate. Preferably, the ratio of calcium carbonate/magnesium carbonate is comprised between 3 and 4.

In a particular embodiment, the present invention relates to a veterinarian composition comprising:
- at least one phosphate binder, in a quantity between 2.5 and 15% w/v, preferably between 2.5 and 10% w/v, more preferably between 4 and 7% w/v;
- at least one uremic toxin binder, in a quantity between 0.5 and 10% w/v, preferably between 0.5 and 5% w/v, more preferably between 0.75 and 2% w/v;
- at least one vasoactive antihypertensive agent, in a quantity between 0.1 and 10% w/v, preferably between 0.5 and 10% w/v, more preferably between 1 and 5% w/v; and
- at least one antifibrotic agent, in a quantity between 0.16 and 3.2% w/v, preferably between 0.5 and 2% w/v, more preferably between 1 and 2% w/v.

In a preferred embodiment, the formulation of the veterinarian composition of the invention is adapted to an oral administration to domestic animals, preferably to carnivore domestic animals, for example dogs and cats. The formulation can be in the form of a tablet, a capsule, a paste, a chewable compound, a liquid, a suspension, or any other form.

Preferably, said formulation will be designed to present an enhanced palatability. Indeed, it is acknowledged that animals, especially cats, are very sensitive to the taste of their food. If the product were to be associated with an unpleasant taste, compliance would become disastrous in a few days. Compliance is key for the success of the treatment which is most of the time a lifelong treatment.

In a specific embodiment of the present invention, the veterinarian composition is an oral appetizing oily suspension; according to this specific embodiment, the physiologically acceptable vehicle comprises:
- an oily vehicle which is an edible oil from animal, vegetable or mineral origin; said oil can be solid or liquid, but is preferably liquid (with a melting temperature of 15° C. or less). The vegetable oils may be soybean oil, coconut oil, palm oil, sunflower oil . . . or their mixture; these oils can also be modified as in the products Miglyol® (sold by the Company SASOL) which are derivatives of fatty acid esters from palm oil or coconut oil, coupled with glycerine or propylene glycol; the animal oils may be cod liver oil, or other fish oil and mineral oil can be paraffin. Preferred oils are vegetable oils. Miglyol®, comprising a triglyceride or a mixture of triglycerides, or a polyol ester; for example, caprylic/capric triglycerides corresponding to the products Miglyol® 810 and Miglyol® 812; or caprylic/capric/linoleic triglycerides corresponding to the product Miglyol® 818; or caprylic/capric/succinic triglycerides corresponding to the product Miglyol® 829; or an oil composed of propyleneglycoldicaprylate/dicaprate corresponding to the product Miglyol® 840;
- at least one gelifying agent selected in the group consisting of aluminum mono-, di- or tristearate; hydrophilic colloidal silica (such as Aerosil 200); Castor Oil hydrogenated (such as Cutina HR or Thixcin R);
- at least one non-ionic tensioactive agent; preferably, stearic acid, polysorbate 80 or Polyoxyethylene (20) sorbitan monooleate;
- at least one antioxidant that include butylhydroxyanisole (BHA), butylhydroxy-toluene (BHT), propylene glycol, propyl gallate, ascorbyl palmitate and a-tocopherol and mixtures thereof; the antioxidant(s) preferably represent from 0.01% to 0.5% approximately (weight/volume);
- at least one material appetizing for the target animal, advantageously chosen from substances of animal or plant origin, such as liver powder, beer yeast, baker yeast, meat meals, fish meals, powdered cheeses or milk derivatives, chicken aroma, anchovy aroma, sucralose, sponge cake aroma and their mixture; the appetizing material is preferably a liver powder. Optionally a flavor enhancer, such as glutamate monosodium, is mixed with said appetizing material.

The present invention thus relates to a veterinarian composition comprising:
- between 1 and 15% w/v of at least one phosphate binder; preferably between 2.5 and 15% w/v, preferably between 2.5 and 10% w/v, more preferably between 4 and 7% w/v;
- between 0.1 and 10% w/v of at least one uremic toxin binder; preferably between 0.5 and 10% w/v, preferably between 0.5 and 5% w/v, more preferably between 0.75 and 2% w/v;
- between 0.16 and 3.2% w/v of at least one antifibrotic agent; preferably between 0.5 and 2% w/v, more preferably between 1 and 2% w/v;
- between 0.1 and 10% w/v of at least one vasoactive antihypertensive agent; preferably between 0.5 and 10% w/v, more preferably between 1 and 5% w/v;
- between 0.1 and 15% w/v of at least one gelifying agent; preferably between 0.5 and 10% w/v, more preferably between 0.75 and 2% w/v;
- between 0.1 and 10% w/v of at least one non-ionic tensioactive agent; preferably between 0.2 and 5% w/v, more preferably between 0.4 and 1% w/v;
- between 0.01 and 0.5% w/v of at least one antioxidant; preferably between 0.01 and 0.1% w/v, more preferably 0.02% w/v;
- between 1 and 30% w/v of at least one material appetizing for the target animal, preferably between 5 and 20% w/v, more preferably between 7.5 and 15% w/v;
- qsp of an edible oily vehicle.

In a preferred embodiment, the veterinarian composition of the invention is as follows:

| | |
|---|---|
| ACE oligopeptides | between 1 and 5% w/v; preferably 2% w/v |
| Polysaccharides extracted from *Astragalus membranaceus* | between 1 and 2% w/v; preferably 1.6% w/v |
| Calcium carbonate | between 1 and 5% w/v; preferably 3.75% w/v |
| Magnesium carbonate | between 0.5 and 2% w/v; preferably 1% w/v |

| | | |
|---|---|---|
| Chitosan | between 0.75 and 2% w/v; preferably 1% w/v | |
| Hydrophilic colloidal silica | between 0.75 and 2% w/v; preferably 1% w/v | |
| Antioxidant | between 0.01 and 0.1%; preferably 0.02% w/v | |
| Liverpowder | between 7.5 and 15% w/v; preferably 10% w/v | |
| Non-ionic tensioactive agent | between 0.4 and 1% w/v; preferably 0.5% w/v | |
| Modified vegetable oil | Qsp 100% | |

The veterinarian composition of the invention is obtained by successively mixing in the oily vehicle: the antioxidant, the anionic tensio-active agent, the gelifying agent, the phosphate binder, the vasoactive hypertensive agent, the uremic toxin binder, the antifibrotic agent and the appetizing material; the order of introduction of the phosphate binder, the vasoactive hypertensive agent and the uremic toxin binder can be modified.

The veterinarian composition of the invention is particularly useful as veterinarian medicine, especially for inducing a decrease of plasma creatinine concentration and, more generally, for preventing and/or treating high blood pressure and/or progressive renal diseases in domestic animal.

Progressive renal diseases include chronic kidney diseases (CKD), chronic renal failure (CRF), chronic renal disease, kidney insufficiency, kidney failure, azotemia . . . .

This veterinarian composition can be used in both animals, dogs and cats with associated hypertension or not, in order to support their kidney function, to reduce the progressive loss of kidney function and to control/decrease hypertension when associated hypertension. More specifically, said composition is particularly adapted to asymptomatic, pre-symptomatic and symptomatic animals, preferably animals being older than 7 years and/or after diagnosis of CKD, with or without associated hypertension; furthermore, predisposed breeds (eg for cats: Persians) may use the veterinarian composition of the invention even before the recommended threshold age.

The beneficial effect of the veterinary composition of the invention lies in the reduction of undesirable adaptive processes and functional changes related to progressive nephron loss in patients with CKD, maintaining normal blood pressure, decrease of intestinal absorption of phosphorus, limitation of uremic toxins accumulation and the improvement of the quality of life of the animal.

The administration of the composition of the invention may be associated with other active agents (ACE inhibitors for example) and/or a specific diet.

In a preferred embodiment, the veterinarian composition is a food supplement, also called nutraceutical or a non feed supplement, which is administered orally, preferably added to the animal's food, daily or twice daily.

The veterinarian composition is preferably conditioned in adapted packaging, for example in a bottle, optionally with a dosage pump device, an adapted syringe or in single-dose pipettes. The volume of the bottle will be adapted to the dose to administer, for instance 50 ml, 60 ml, 100 ml, 180 ml, 250 ml, or 300 ml bottles.

The amount of veterinarian composition to be administered may range from 0.1 to 5 ml approximately, preferably from 1 to 3 ml approximately for cats and from 2 to 5 ml approximately for dogs, as a function of the weight of the animal under consideration and the dosage.

It should be clearly understood that the following examples are given purely as illustrations of the subject of the invention, of which they do not in any way constitute a limitation.

EXAMPLES

I. Preparation of a Veterinarian Composition According to the Present Invention

The following composition

| Substance: | Quantity (% p/v) | Content in 1 ml | Function |
|---|---|---|---|
| Active agents | | | |
| ACE oligopeptides | 2 | 20 mg | Vasoactive anti-hypertensive agent |
| Polysaccharides extracted from *Astragalus membranaceus* | 10 | 100 mg | Antifibrotic agent |
| Calcium carbonate | 3.75 | 37.5 mg | Phosphate binder |
| Magnesium carbonate | 1 | 10 mg | Phosphate binder |
| Chitosan | 1 | 10 mg | Uremic toxin binder |

-continued

| Substance: | Quantity (% p/v) | Content in 1 ml | Function |
|---|---|---|---|
| Excipient(s) | | | |
| Hydrophilic colloidal silica | 1 | 10 mg | Gelifying agent |
| BHT | 0.02 | 0.2 mg | Antioxidant |
| Liver powder | 10 | 100 mg | Appetizing material |
| Polyoxyethylene (20) sorbitan monooleate | 0.5 | 5 mg | Non ionic tensioactive agent |
| Miglyol | Qs 100 | Qs 1 ml | Oily vehicle | is prepared as described below:

Equipment needed: a stainless steel tank and a system of rotor-stator dispersion.

Operating protocol:

In a suitable vessel: introduce all Miglyol; introduce then sequentially BHT, Polyoxyethylene (20) sorbitan monooleate, hydrophilic colloidal silica, Calcium Carbonate, Magnesium Carbonate, the ACE oligopeptides, Chitosan, the extracts of *Astragalus membranaceus* (Astragalus Root) and the liver powder, disperse until obtaining a homogeneous product.

II. Assessment of the Effect of the Administration of the Veterinarian Composition of Example I Materials and Methods Animal Selection Prior to the study 10 adult healthy cats, 5 males and 5 females were selected randomly. At the day 0 of the study animals were aged from 2 to 5 years. Animals were fed by industrial food only; no changes in nutrition were recorded past 12 months. Animals were located in specialised centre for animal experimentation.

The composition of example I was administered orally during 12 weeks at normal dose 0.5 ml per 1 kg of body weight and per day; it was given in one single administration in the morning before the meal.

Biological Analysis

Blood and urinary sampling, as well as clinical examination, body weight measurement were performed in the morning before feeding. Biological analyses were performed at four check-points (t0, t0+7 days, t0+42 days, t0+84 days). Next variables were considered: Blood urea nitrogen (BUN), serum creatinine (SCr), serum inorganic phosphorus (P), serum magnesium (Mg), serum calcium (Ca), urinary protein to creatinine ratio (UPC), urinary fractional excretion of phosphorus (UP %), urinary specific gravity (Ud).

Statistical Analysis

Analysing of the data was performed using SAS 9.2 software.

The biochemical parameters were compared between D0 and D84 using a paired t-test or a Wilcox on signed ranks tests at the 5% significance threshold. In order to test correlation between the parameters urea, creatinine, phosphorus and weight on D0, Pearson coefficients of correlation were computed and tested at the 5% significant threshold.

Results

Blood and urine samples were collected from all cats at T0, T0+7 days, T0+42 days and T0+84 days. FIGS. 1 to 6 represents results of blood analysis in cats.

Figure 4:
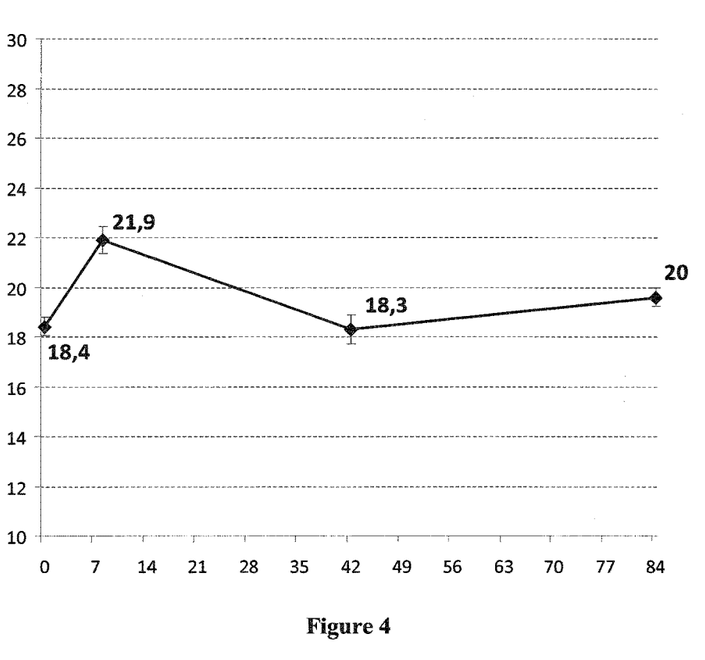
FIG. 4 is a graph representing mean magnesium serum in mg/l with SEM concentrations in cats that received the tested composition (formulated as in example I) during 84 days. The concentration in mg/l is represented in ordinate whereas the time is represented in days in abscissa.
Figure 5:
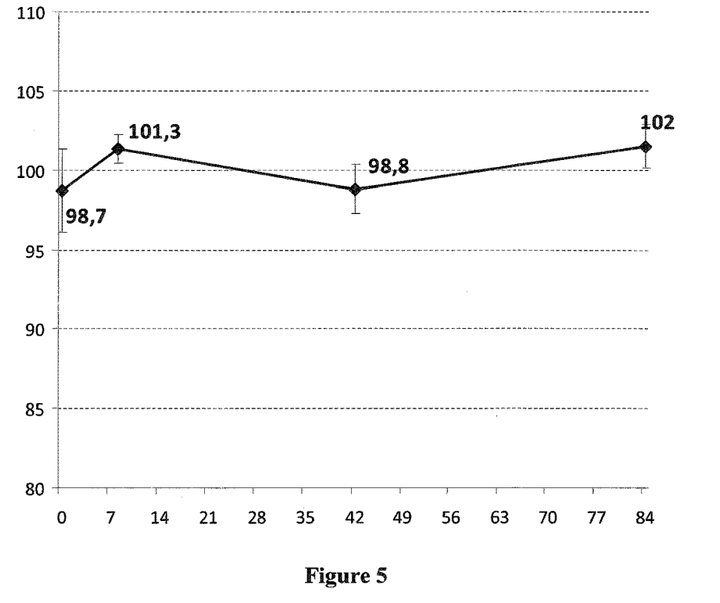
FIG. 5 is a graph representing mean calcium serum in mg/l with SEM concentrations in cats that received the tested composition (formulated as in example I) during 84 days. The concentration in mg/l is represented in ordinate whereas the time is represented in days in abscissa.

Safety Parameters of the Tested Composition:

Over the period of the study, all Ca and Mg blood levels remained within normal ranges in all animals supplemented with the tested composition (FIGS. 4 and 5). In particular, due to a theoretical concern regarding the possible induction of hypocalcaemia, no statistically significant changes were recorded in calcium blood levels ($p=0.19$) when comparing day 0 to day 84.

Figure 1:
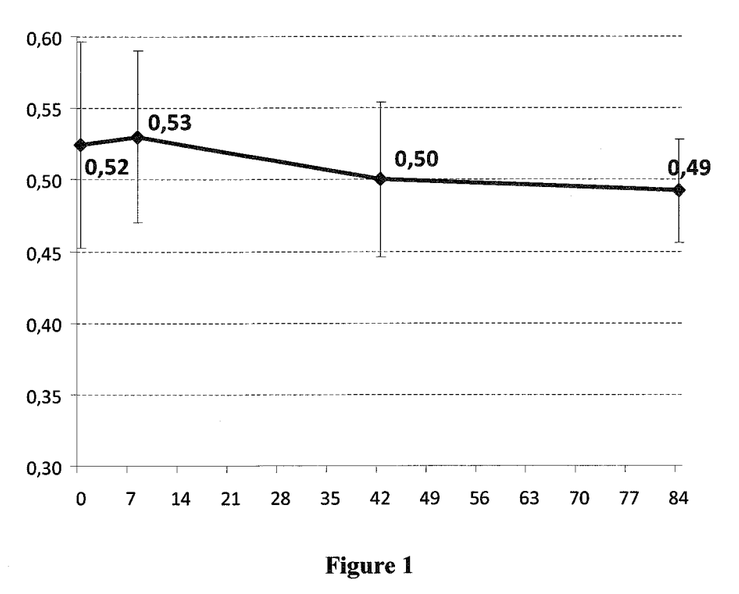
FIG. 1 is a graph representing mean blood urea nitrogen (BUN) concentrations in g/l (with standard error of the mean, SEM) in cats that received the tested composition (formulated as in example I) during 84 days. The concentration in g/l is represented in ordinate whereas the time is represented in days in abscissa.
Figure 2:
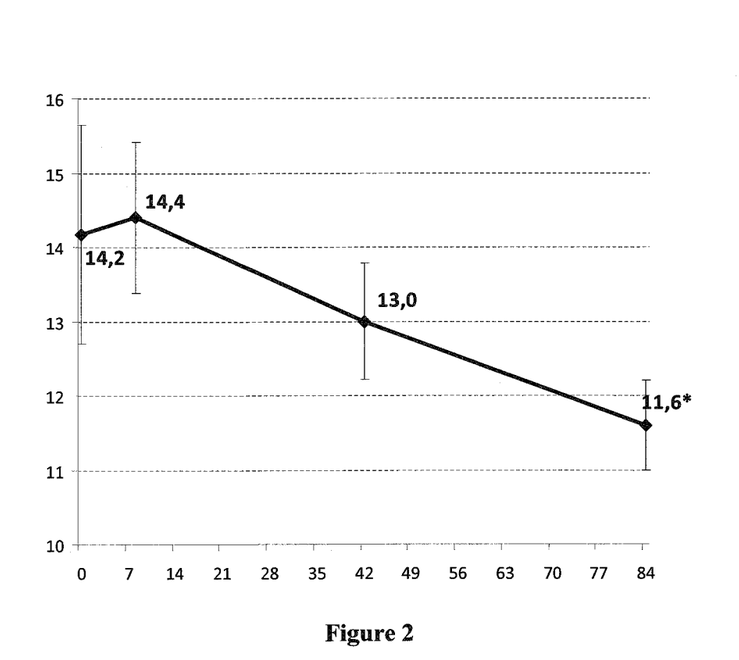
FIG. 2 is a graph representing mean creatinine serum in mg/l with SEM concentrations in cats that received the tested composition (formulated as in example I) during 84 days (*p<0.05 compared to the beginning of the study at day 0). The concentration in mg/l is represented in ordinate whereas the time is represented in days in abscissa.
Figure 3:
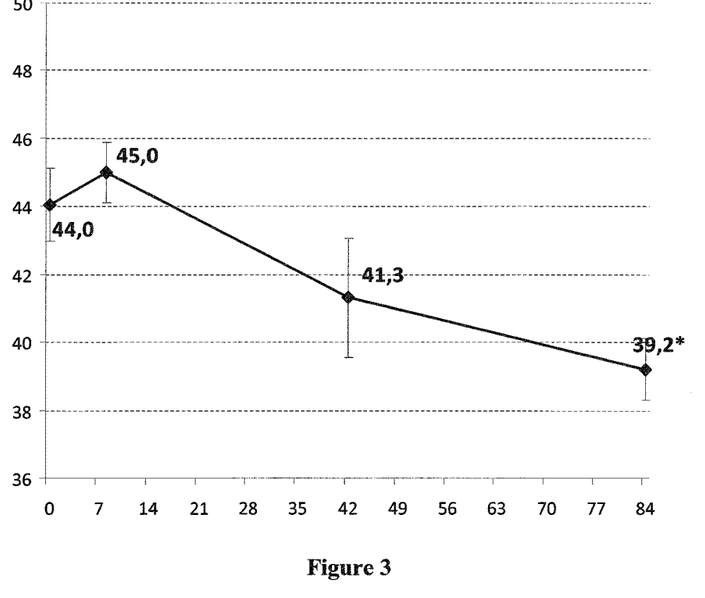
FIG. 3 is a graph representing mean inorganic phosphorus serum concentrations in mg/l with SEM in cats that received the tested composition (formulated as in example I) during 84 days (*p<0.05 compared to the beginning of the study at day 0). The concentration in mg/l is represented in ordinate whereas the time is represented in days in abscissa.

Efficacy Parameters of the Tested Composition:

Over the study period (day 0 compared with the day 84) animals supplemented with the tested composition had statistically significant decrease of inorganic phosphorus with p value equal 0.002 (FIG. 3). During the same period of time animals had statistically significant decrease of creatinine, with p values equal 0.016 (FIG. 2). BUN serum levels also decreased over study period time. Fractional excretion of phosphorus was statistically lower at the end of the study than in the begging ($p=0.02$).

Figure 6:
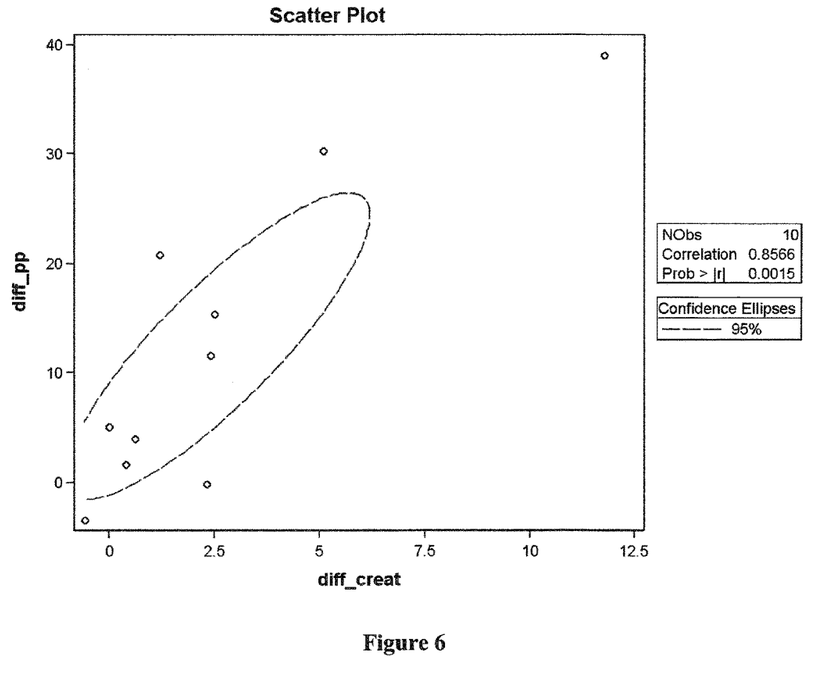
FIG. 6 is a graph (scatter plot) representing the correlation between serum creatinine levels (diff creatinine in abscissa) and urinary fractional excretion of phosphorus (diff phosphorus excretion in ordinate) in cats that received the tested composition (formulated as in example I) during 84 days. The 95% confidence ellipse is represented in dotted line. The Pearson coefficient of correlation is 0.8566 (close to 1) (number of observations 10, Prob>|r| 0.0015), so one can state that the serum creatinine levels and urinary fractional excretion of phosphorus in cats are correlated.
Figure 7:
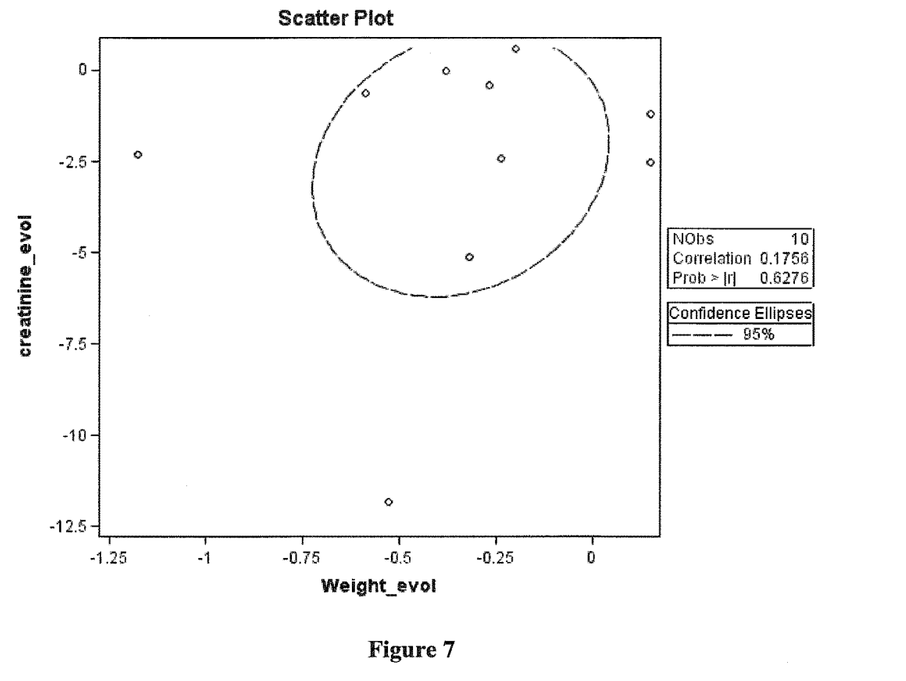
FIG. 7 is a graph (scatter plot) representing no correlation between evolution of serum creatinine levels (evolution of creatinine level in ordinate) and weight in cats (evolution of weight in abscissa) that received the tested composition (formulated as an example I) at day 0 and at day 84. The 95% confidence ellipse is represented in dotted line. The Pearson coefficient of correlation is 0.1756 (number of observations 10, Prob>|r| 0.6276), so one can state that the evolution of the serum creatinine levels and weights of the cats are not correlated.

Statistical Correlation:

Significant correlation were found ($p=0.002$) between changes in creatinine blood values and the changes in values of urine fractional excretion of phosphorus between day 0 and day 84 (FIG. 6). The same conclusion was obtained with a nonparametric test. Changes in blood creatinine levels and urea blood nitrogen levels were also found to be statistically correlated between day 0 and day 84 (0.038 for the group of animals involved in the study. No statistical correlation was found between changes in other parameters, including changes in body weight and creatinine blood levels over study period of time (FIG. 7).

Discussion

This trial provided data on safety and efficacy of use in vivo new complementary feed according to the invention containing an association of combined phosphate binders with other natural active substances. The tested composition have been proven to be efficient in lowering serum phosphorus concentration as well as in lowering blood urea nitrogen. More importantly, and reported for the first time, is the lowering of serum creatinine levels, which are considered as an important prognostic factor of renal health. This outstanding result has furthermore been obtained without inducing pathological hypercalcemia or hypermagnesaemia in the animals.

As an additional benefit this in-vivo trial provided data of safety of use calcium and magnesium phosphate binders in feline specie; over 12-week use of the supplement there was no statistically significant changes in magnesium and calcium blood levels. In the course of this study we did not establish the long-term effects of the use of a maintenance diet plus intestinal phosphorus binder on the preservation of renal structure and function in cats, however for the first time an in-vivo trial have shown that association of phosphate binders with other reno-protectant substances will not only generate a decrease in phosphataemia, but improve other important prognostic factors of chronic renal disease such as creatinaemia. Phosphate binders-only use has been previously proven to not change levels of serum creatinine. Thus a significant decrease in creatinine serum levels could not be attributed to phosphate binders, but really to their association with other natural reno-protectant substances.

The invention claimed is:

1. A method of treating a domestic animal for high blood pressure and/or progressive renal disease, the method comprising administering an association comprising at least one phosphate binder, at least one uremic toxin binder, at least one vasoactive anti-hypertensive agent and at least one antifibrotic agent sufficient to induce a decrease in serum creatinine concentration in the domestic animal; wherein the association comprises a mixture of calcium carbonate and magnesium carbonate in the ratio of calcium carbonate to magnesium carbonate of between 3:1 and 4:1, and wherein the domestic animal is a cat.

2. The method of claim 1, wherein the association is administered to the domestic animal once or twice daily.

3. A method of treating chronic kidney disease (CKD), chronic renal failure (CRF), chronic renal disease, kidney insufficiency, kidney failure or azotemia in a domestic animal, the method comprising administering an association comprising at least one phosphate binder, at least one uremic toxin binder, at least one vasoactive anti-hypertensive agent and at least one antifibrotic agent sufficient to induce a decrease in serum creatinine concentration in the domestic animal; wherein the association comprises a mixture of calcium carbonate and magnesium carbonate in ratio of calcium carbonate to magnesium carbonate of between 3:1 and 4:1, and wherein the domestic animal is a cat.

4. The method of claim 3, wherein the association is administered to the domestic animal once or twice daily.

\* \* \* \* \*